United States Patent [19]
Birch et al.

[11] Patent Number: 5,869,972
[45] Date of Patent: Feb. 9, 1999

[54] TESTING DEVICE USING A THERMOCHROMIC DISPLAY AND METHOD OF USING SAME

[76] Inventors: Brian Jeffrey Birch, 14 Duchy Close, Chelveston, Northamptonshire, England, NN9 6AW; Edward Baginski, 41 Oakpits Way, Rushden, Northamptonshire, England, NN10 0PP; Nicholas Andrew Morris, 71 Spring Road, Kempston, Bedford, Bedfordshire, England, MK42 8LT; Catherine Lovell, 23A Castle Road, Bedford, Bedfordshire, England, MK40 3LP; Michael Catt, 14 Brampton Close, Wellingborough, Northamptonshire, England, NN8 5XG; Miles Hugh Eddowes, 42 Portland Street, St. Albans, Hertfordshire, England, AL3 4RA

[21] Appl. No.: 807,008
[22] Filed: Feb. 26, 1997
[30] Foreign Application Priority Data
Feb. 26, 1996 [EP] European Pat. Off. .............. 96301259
[51] Int. Cl.⁶ ........................... G01N 33/18; G01N 33/48
[52] U.S. Cl. ......................... 324/439; 324/441; 324/450; 250/564; 422/56; 422/82.02
[58] Field of Search ................................ 324/438, 439, 324/450, 692, 693, 713, 717, 722; 422/55, 56, 82.01, 82.02, 82.05; 436/66, 67, 68, 169; 250/564; 128/632, 633, 636, 637, 748, 771; 204/400, 402, 403; 600/309, 365, 367, 368, 561, 584

[56] References Cited

U.S. PATENT DOCUMENTS

| | | | |
|---|---|---|---|
| 4,882,492 | 11/1989 | Schlager | 250/346 |
| 5,174,963 | 12/1992 | Fuller et al. | 422/82.05 |
| 5,179,288 | 1/1993 | Miffitt et al. | 250/564 |
| 5,200,706 | 4/1993 | Yada | 324/450 |
| 5,597,532 | 1/1997 | Connolly | 422/56 |

FOREIGN PATENT DOCUMENTS

| | | |
|---|---|---|
| 0 170 375 | 2/1986 | European Pat. Off. . |
| 0 212 314 | 3/1987 | European Pat. Off. . |
| 0 308 770 | 3/1989 | European Pat. Off. . |
| 0 127 958 | 12/1994 | European Pat. Off. . |
| 4324679 | 1/1995 | Germany . |
| WO 87/06692 | 11/1987 | WIPO . |
| WO 91/11530 | 8/1991 | WIPO . |
| WO 95/28645 | 10/1995 | WIPO . |
| WO 96/13707 | 5/1996 | WIPO . |

*Primary Examiner*—Josie Ballato
*Assistant Examiner*—Diep Do
*Attorney, Agent, or Firm*—Pillsbury Madison & Sutro LLP

[57] ABSTRACT

A testing device for qualitatively or quantitatively sensing an electrochemical or analogous reaction at the surface of a test strip (46), the current flowing or charge accumulated at the test strip being processed by electronics (50) to generate a current signal suitable for activating a display (52) typically in the form of a thermochromic layer.

12 Claims, 4 Drawing Sheets

CONC 1 > CONC 2 > CONC 3

TESTING DEVICE USING A THERMOCHROMIC DISPLAY AND METHOD OF USING SAME

FIELD OF THE INVENTION

This invention relates generally to determination of the characteristics of fluids (liquids or gases) and more specifically to a qualitative or quantitative method of testing for such a characteristic and to a testing device for use in determination of the characteristic.

The term "characteristic" is used herein in its most general sense to refer to any qualitative or quantitative physical or chemical property of a fluid which may require to be determined, including for example the presence or absence of a particular constituent in the fluid or the concentration of a particular constituent in the fluid.

THE INVENTION

According to one aspect of the invention there is provided a testing device for use in determination of a particular characteristic of a fluid, the device comprising a sensing element for contacting the fluid and producing a response indicative of the characteristic to be determined; electronic means for processing the response to produce an electrical signal of magnitude indicative of the characteristic; and indicator means which responds to a change in magnetic field, electric field, voltage, polarisation or transmission of light, or temperature resultant from the electrical signal, thus producing a visible indication of the magnitude of the electrical signal and hence of the characteristic of interest.

According to a second aspect of the invention, there is provided a method of testing a fluid for a particular characteristic thereof using a testing device, comprising contacting the fluid with the testing device to cause a sensing element of the device to produce a response indicative of the characteristic to be determined, electronically processing the response in the device to produce an electrical signal, the magnitude of which is indicative of the characteristic, and which causes a visually discernable change in indicator means of the device which responds to a change in magnetic field, electric field, voltage, polarisation or transmission of light, or temperature resultant from the electrical signal, thus producing a visible indication of the magnitude of the electrical signal and hence of the characteristic of interest.

The invention lends itself well to embodiments in the form of portable testing devices, possibly hand-held testing devices.

The testing device generally requires a source of electrical power for operation. The power source may form part of the device, and may for instance be a small battery, for example a lithium cell or an air cell such as a zinc-air cell, or a solar cell, for example based on amorphous or crystalline silicon and optionally used in conjunction with an electrical storage device such as a capacitor. Alternatively, the power source may be derived from the fluid sample under test, with electrolytic fluids such as gastric juices and possibly urine acting as electrolyte for a battery.

The sensing element will typically take one of two main forms. In the first form, a change in electrical potential between two electrodes is measured under near zero current conditions. In the second form, a current flow is measured as a result of an electrochemical process taking place at surfaces of one or more electrodes. In both of these forms the electrical signals are indicative of the characteristic of interest, eg concentration of glucose in blood. The sensing element may carry an enzyme, immunochemical or other substance which promotes the electrochemical reaction. Again, the sensing element may carry a miniature light source and detector which qualitatively or quantitatively senses the presence of a constituent of the fluid by optical detection.

The electronic response-processing means may also take various forms, such as a simple integrated circuit, or an amplifier circuit, practised as conventional electrical circuitry.

This electronic means, whatever its form, in use receives the signal from the sensing element and converts it into a form compatible with the manner of operation of the indicator means, or display.

The indicator means itself may also take various forms, such as a thermochromic strip, a strip which otherwise changes its appearance, eg. colour or reflectance, with temperature change or in the presence of an electric field, a conductive strip of continuous or stepped variable resistance, discretely variable resistances, light emitting polymers, or possibly LEDs and LCD devices based upon changes in transmittance or polarisation of light.

For the indicator means to be responsive to the electrical signal, the indicator means generally needs to be in close proximity to the electronic means.

The thermochromic or other strip, when employed, may be of the irreversible kind, so as to provide a record of the result of the test which can be retained, or may be of the reversible kind to allow for reuse of the display.

Thus, the complete testing device may be embodied in various ways. In one embodiment, the testing device is wholly disposable; in another, the sensing element and indicator means are separable and disposable (or retainable as a record); and in another, the sensing element only is disposable (or retainable as a record).

In all these embodiments, the sensing element may comprise a test strip in the form of a base layer, conductive tracks laid over the base layer, e.g. to form electrodes, a thermochromic layer deposited over the conductive tracks, i.e. to respond, after amplification, to current flow in the conductive tracks, and a covering layer over the thermochromic layer.

In a particular aspect the invention provides a method of testing a fluid for a particular characteristic thereof according to which a hand-held testing device is contacted with the fluid to cause a powered sensing element to produce a response indicative of the characteristic to be determined, any response is processed to produce an electrical signal, the magnitude of which is indicative of the characteristic, in close proximity to means which responds to a change in electric field or in temperature resultant from the electrical signal to produce a visible indication of the magnitude of the electrical signal.

In another specific aspect the invention provides a portable tester for use in determination of a particular characteristic of a fluid, comprising a hand-held device for contact with the fluid, the device comprising a source of electrical power, a sensing element which when powered has a response to the said characteristic if present in the fluid to produce a response, electronic means for processing the response to produce an electrical signal of magnitude indicative of the characteristic, and in close proximity to the electronic means an indicator which responds to a change in electric field or temperature resultant from the electrical signal in a visually discernable manner.

DESCRIPTION OF EMBODIMENTS

The invention is further described, by way of illustration, with reference to the accompanying drawings, in which:

FIGS. 1(a–c) diagrammatically indicates three possible designs of a portable tester in accordance with the invention, incorporating a solid state display;

DETAILED DESCRIPTION OF THE DRAWINGS

Figure 1A:
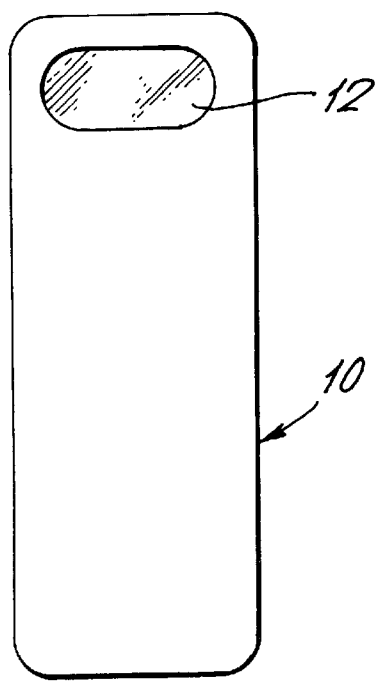

FIG. 1(a) shows an integral design of portable tester 10 which is disposable in its entirety after use. Reference 12 indicates the display or indicator means.

Figure 1B:
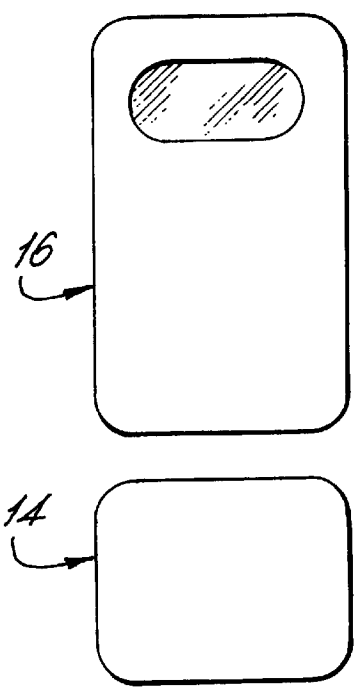

In the split design of FIG. 1(b), the sensing element in the form of test strip 14 is disposable after use of the tester, whilst the main body 16 comprising the power cell, electronics and display is retained for re-use, typically for only a limited number of times.

Figure 1C:
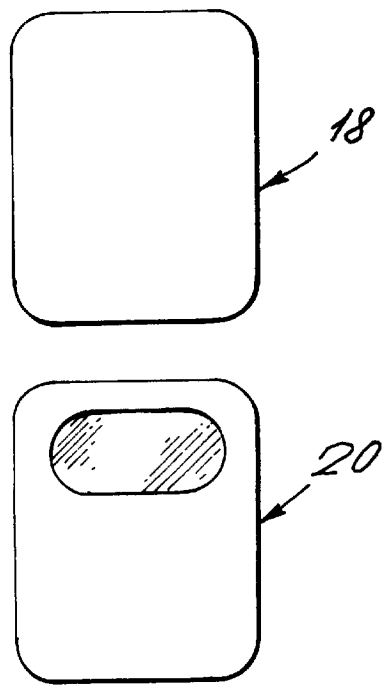

The split design of FIG. 1(c) has re-usable main body 18 comprising the power cell and electronics, whilst the test strip and display, conveniently combined into a single element 20, are disposable.

Figure 2:
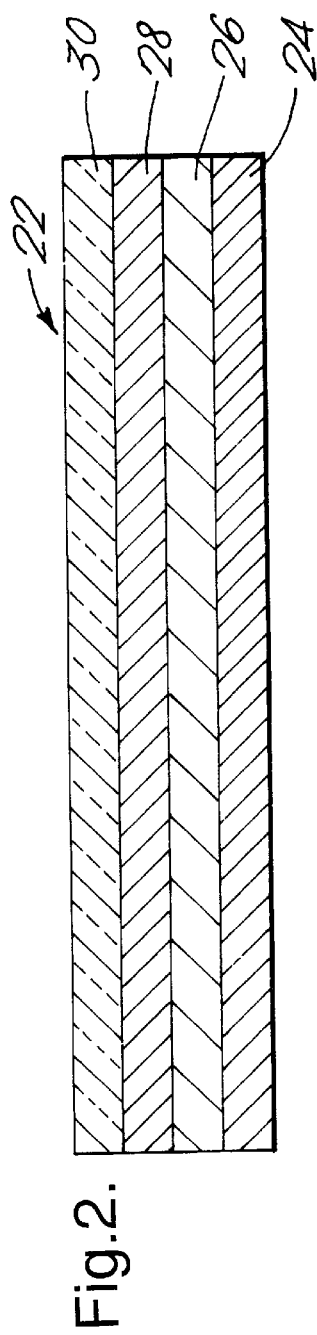
FIG. 2 shows one possible embodiment of sensing element.

The design of FIG. 1(c), which is possibly the preferred design, may conveniently employ a composite test strip 22 of the kind shown in FIG. 2. This test strip comprises a base layer 24 bearing conductive tracks 26, a thermochromic layer 28 deposited over the conductive tracks, and a transparent covering layer 30. When current passes in the conductive tracks 26, a portion of the thermochromic layer changes colour, the dimensions of the changed colour portion being dependent on the magnitude of the current, which is suitably processed and/or amplified by the electronics in the main body of the tester. An additional advantage can be introduced by placing a thin layer of heat conducting and coloured material between the electrodes and the thermochromic layer so that in cases where the layer turns transparent the quantification could be visually read by a colour change as well as position by heatinduced change in the thermochromic layer.

Figure 3:
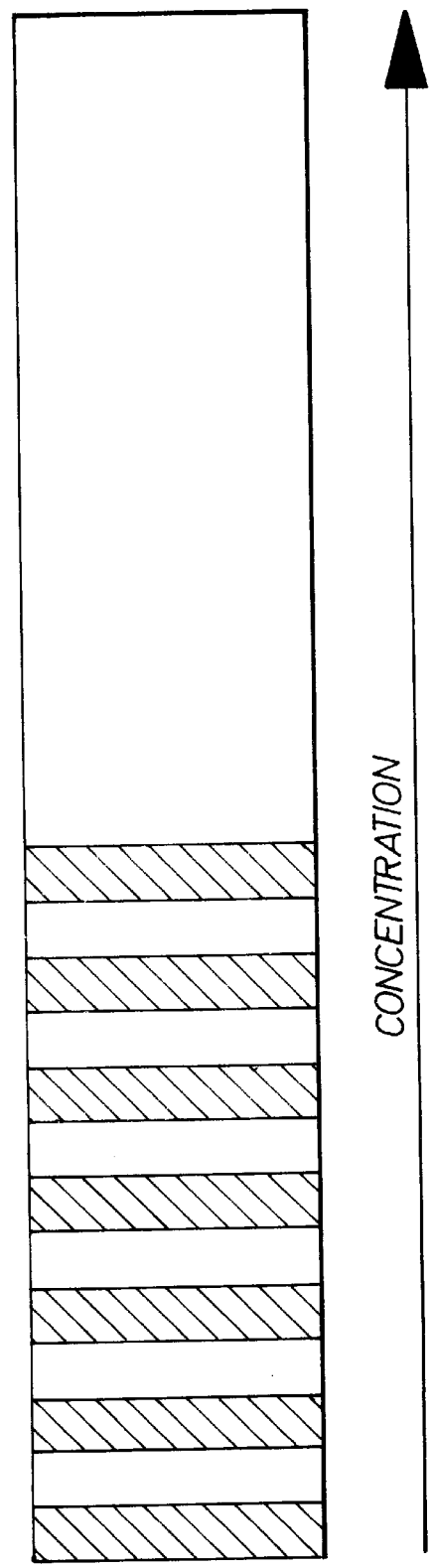
FIG. 3 shows one possible form of the indicator means when the tester is employed to quantitatively detect the concentration of an analyte in a fluid.

FIG. 3 indicates one possible form of display. If the tester is used quantitatively to sense the concentration of analyte in a solution, the number of bars which are revealed, as by change of colour for example, is proportional to the analyte concentration.

Figure 4:
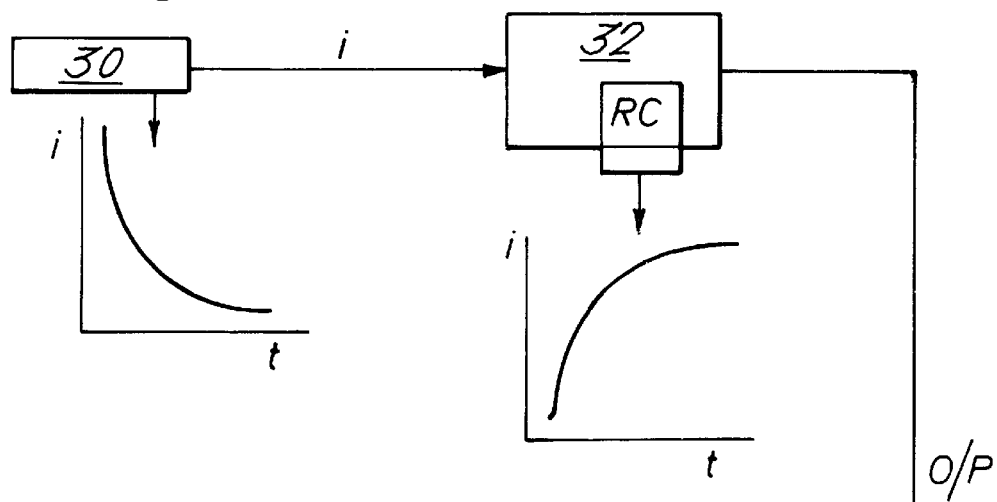
FIG. 4 is an explanatory diagram.
Figure 4:
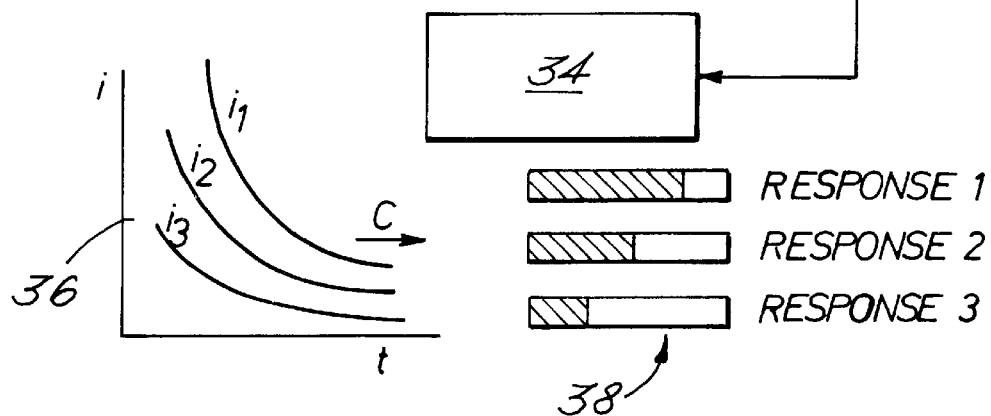

FIG. 4 is a diagram for use in understanding the functions of the tester.

At the test strip 30, the current i (or charge q) generated is dependent on, for example, the concentration of the analyte in a solution. The current (or charge) signal (the response) is processed in electronics 32, conveniently including a capacitor in which the current or charge is integrated. A predefined decay is determined by the magnitude of a resistor in an RC circuit of which the capacitor forms part. The electronics provides an output in a form acceptable to the display 34. In the drawing, the graph 36 shows three possible current curves for concentration 1>concentration 2>concentration 3 which may be received at the display 34, which in this case provides a continuous bar output 38 of length dependent on the concentration of the analyte. The actual display could be digital, i.e. in discrete steps, instead of analogue, i.e. continuous.

If the test strip accumulates charge q, the electronics may be designed to produce a constant current output the magnitude of which is proportional to the magnitude of stored charge.

Figure 5:
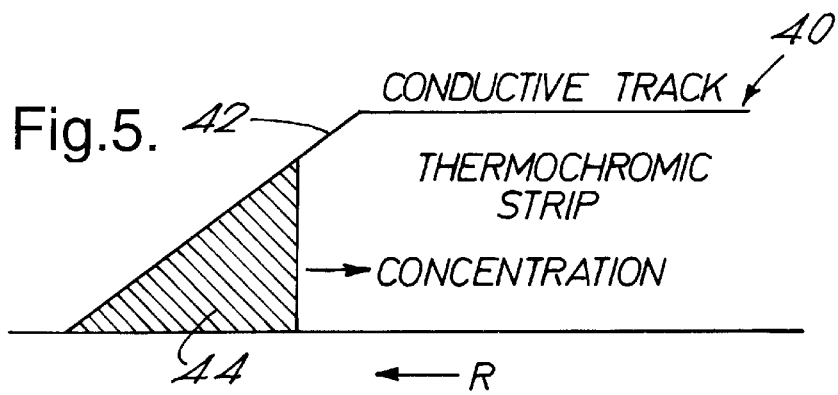
FIG. 5 shows another possible form of the indicator means, when this takes the form of a thermochromic strip.

FIG. 5 again shows one possible form of display 40 in the form of a thermochromic strip. As the current increases in the conductive track 42, so the area 44 of the thermochromic layer which changes in colour is increased, and this moves to the right as depicted due to a variation in response.

Figure 6:
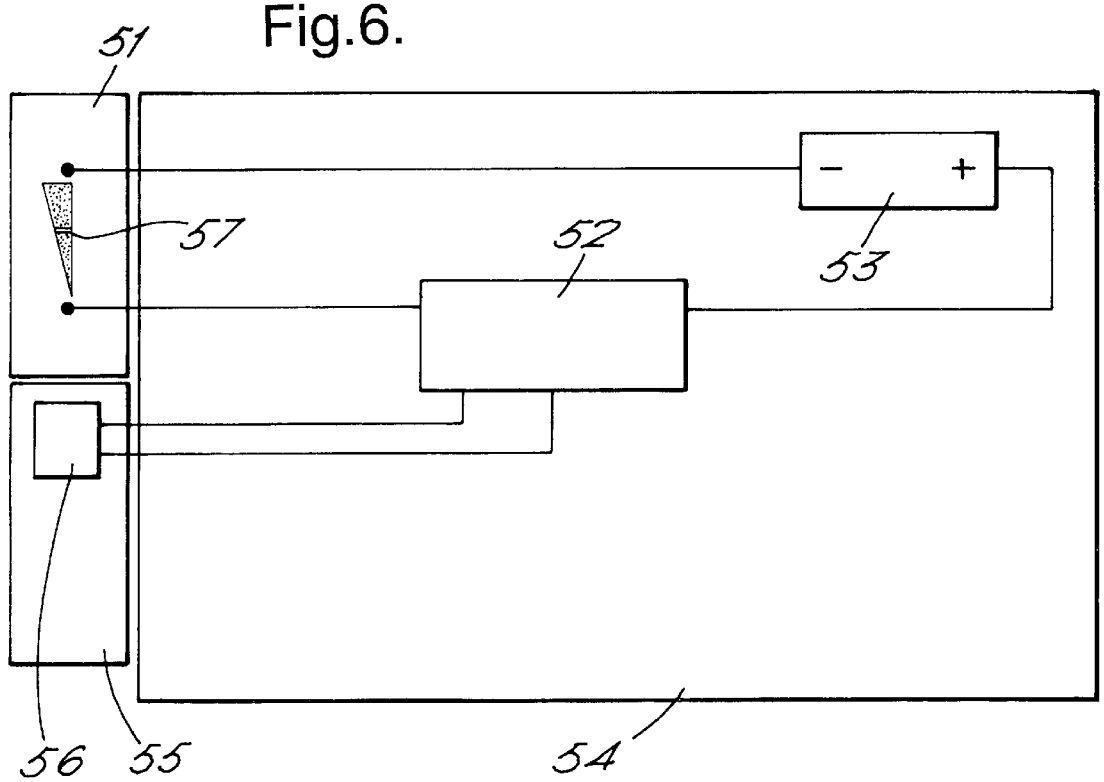
FIG. 6 is a simplified circuit diagram of one embodiment of testing device in accordance with the invention.

FIG. 6 illustrates schematically one embodiment of testing device in accordance with the invention. In FIG. 6, the illustrated embodiment comprises two separable parts: a first part 54 in which are housed a reusable power supply 53 and an electronics element 52; and a second part comprising a display module 51 and a sensing module 55. The display module contains a disposable display element 57 of the form described in connection with FIG. 2. The sensing module 55 contains an electrode arrangement 56 in the form of a capillary fill device (CFD) comprising a pair of spaced apart plates defining a cavity of known volume and capable of filling by capillary action, with electrodes within the cavity, eg as disclosed in EP 0170375.

In use, a known volume of fluid to be tested is introduced to CFD 55 by capillary action. An electrical potential is applied across the electrodes of the CFD, resulting in a flow of current through the sample fluid proportional to the electrochemical activity. Integration of the electrochemical current over a substantial period of time relative to the activity rate results in a measurement of the total number of moles of electroactive species in the known volume of sampled fluid. To this end, electronics element 52 includes an electronic integrator in which charge is collected. The charge collected could be discharged instantaneously through an irreversible thermochromic strip 57, resulting in an indication of the amount of charge integrated. Amplification (or attenuation) of the signal at this stage, or prior to integration, is possible when using low (or high) levels of signal. The timing of this event could be initiated by a measurement of the electrochemical activity relative to the initial rate measured at the beginning of the integration period, for example when the signal falls to 99.5% of the initial rate. Alternatively initiation could be after a fixed time period within the integration process. Electrochemical activity could be, for example, a conventional system such as the established glucose oxidase enzymatic systems for glucose measurements.

Alternatively, an electronic amplifier system could be used to boost the electrochemical current and display the current through the thermochromic strip 57 in a continuous manner.

As a further possibility, the current flowing through a series circuit of power source and electrodes immersed in analyte could be passed through a current to voltage converter and then the varying output applied to a liquid crystal or similar electrochromic display. Additionally the current to voltage converter could be substituted for a current integrator and the constant voltage present at the output at the end of the integration period applied to the electrochromic indicator.

Figure 7:
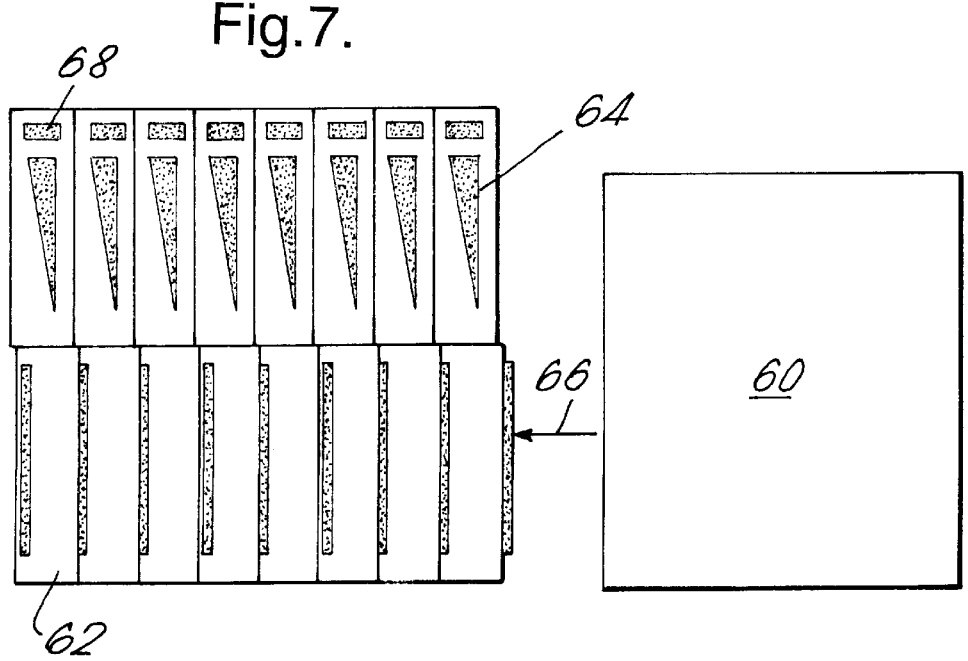
FIG. 7 illustrates schematically a modular embodiment of the invention.

FIG. 7 illustrates schematically a modular embodiment of the invention, comprising a reusable unit 60, which corresponds generally to part 54 of FIG. 6 and comprises a power source and electronics element; and an array of disposable sensing modules 62 each with an associated display module 64, which correspond generally to modules 51 and 55 of FIG. 6. In use, unit 60 is connected to the sensing module and associated display module at one end of the array, as illustrated schematically by arrow 66, and the test is performed as described above. The modules used may then be separated from the remainder of the array. The sensing module will generally be disposed of after use, and the display module may either be disposed of with the sensing module or may be separated from the sensing module and retained for record purposes. To this end, the display modules each carry a unique, preferably machine-readable, identifier 68 such as a bar code. The bar code could be read by the electronic components and recorded in a computer readable format for additional processing be the said electronics or by external facilities. The bar codes could incorporate a code to identify the analytes that can be measured or the actual performance characteristics of the particular batch being used. Instead of bar codes other known forms of coding such as shades of colour, diffracting grating characteristics or passive electronic components or others known to those skilled in the art could alternatively be used.

The tester may be employed for a variety of purposes, such as sensing oxido-reductase reactions which result in current flow or changes in chemical potential at electrode surfaces. Examples are GODFAD/FADH2, or enzymes which employ NAD/NADH2 or NADP/NADPH2 systems. In potentiometry, it is possible qualitatively or quantitatively to sense any chemical reaction which changes the electrochemical potential at the surface of an electrode in a manner that reflects the concentration of the analyte. This could include schemes based upon inhibition principles as well as the usual forms of determination. It is possible for the test strip to carry a substance which promotes the reaction (when the test strip is disposable). The electro-chemical reaction may be associated with antibody-antigen reactions (Ab-Ag) for electrochemical linked immuno assays.

Moreover, the tester can be applied to optical assay systems, such as in any of the foregoing examples, but with optical detection and transduction.

We claim:

1. A testing device for use in determination of a particular characteristic of a fluid, comprising a sensing element for contacting the fluid and producing a response indicative of the characteristic to be determined, electronic means for processing the response to produce an electrical signal of magnitude indicative of the characteristic, and a display device comprising a conductive track for passing a current the magnitude of which is dependent on the magnitude of the electrical signal produced by the electronic means and a thermochromic layer overlying the conductive track for changing color to a dimensional extent dependent on the magnitude of current passing in the conductive track.

2. A testing device according to claim 1, in the form of a portable device.

3. A testing device according to claim 2, in the form of a hand-held device.

4. A testing device according to claim 1, further comprising a source of electrical power.

5. A testing device according to claim 1, wherein at least the sensing element is separable from the remainder of the testing device and is disposable.

6. A testing device according to claim 1, wherein the sensing element carries a promoter for stimulating an electrochemical reaction at the surface of a test strip.

7. A testing device according to claim 1, wherein the display device includes a thin layer of colored material becoming transparent with generation of heat, located between the conductive track and the thermochromic layer.

8. A testing device according to claim 1, wherein the thermochromic layer is adapted to provide an analogue read-out in the form of a bar the length of which is dependent on the magnitude of the current passing through the conductive track.

9. A testing device according to claim 1, wherein the thermochromic layer is adapted to provide a digital read-out in the form of a number of discrete steps which is dependent on the magnitude of the current passing through the conductive tracks.

10. A method of testing a fluid for a particular characteristic thereof using a testing device, comprising the steps of contacting the fluid with the testing device to cause a sensing element to produce a response indicative of the characteristic to be determined, and electronically processing the response to produce an electrical current the magnitude of which is indicative of the characteristic, characterized by the further step of passing the electrical current through a conductive track underlying a thermochromic layer which thereby changes color to a dimensional extent dependent on the magnitude of the current.

11. A method according to claim 10, applied to test the concentration of an analyte in a solution by sensing an electrochemical reaction at the surface of an electrode on the sensing element.

12. A testing device for use in determination of a particular characteristic of a fluid, comprising a sensing element having electrodes for contacting the fluid, means whereby a current signal is caused to pass between the electrodes when the sensing element is in contact with the fluid, the magnitude of said current signal being representative of the fluid characteristic to be determined, electronic means for processing the current signal to produce a display signal, and a display device for receiving the display signal, whereby to produce a visual indication of the fluid characteristic to be determined, said display device comprising a conductive track for passing the display signal and a thermochromic layer overlying the conductive track for changing color to a dimensional extent dependent on the magnitude of the display signal.

* * * * *